(12) United States Patent
Gundel

(10) Patent No.: US 7,419,573 B2
(45) Date of Patent: Sep. 2, 2008

(54) CIRCUIT FOR ELECTROCHEMICAL SENSOR STRIP

(75) Inventor: Douglas B. Gundel, Austin, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 792 days.

(21) Appl. No.: 10/702,344

(22) Filed: Nov. 6, 2003

(65) Prior Publication Data
US 2005/0098432 A1    May 12, 2005

(51) Int. Cl.
G01N 27/327    (2006.01)

(52) U.S. Cl. .................. 204/403.04; 204/400

(58) Field of Classification Search ..................
204/403.01–403.15, 416–418, 400; 205/777.5, 205/778, 792
See application file for complete search history.

(56) References Cited

U.S. PATENT DOCUMENTS

| | | | |
|---|---|---|---|
| 4,778,758 A | 10/1988 | Ericsson et al. | |
| 4,897,173 A | 1/1990 | Nankai et al. | |
| 5,288,636 A | 2/1994 | Pollmann et al. | |
| 5,437,999 A | 8/1995 | Diebold et al. | |
| 5,708,247 A * | 1/1998 | McAleer et al. | 204/403.05 |
| 5,741,634 A | 4/1998 | Nozoe et al. | |
| 5,759,364 A * | 6/1998 | Charlton et al. | 204/403.14 |
| 5,762,770 A | 6/1998 | Pritchard et al. | |
| 5,820,957 A | 10/1998 | Schroeder et al. | |
| 5,981,203 A | 11/1999 | Meyerhoff et al. | |
| 5,997,817 A | 12/1999 | Crismore et al. | |
| 6,096,247 A | 8/2000 | Ulsh et al. | |
| 6,175,752 B1 | 1/2001 | Say et al. | |
| 6,287,451 B1 | 9/2001 | Winarta et al. | |
| 6,488,828 B1 * | 12/2002 | Bhullar et al. | 204/403.01 |
| 6,923,894 B2 * | 8/2005 | Huang et al. | 204/403.06 |

(Continued)

FOREIGN PATENT DOCUMENTS

DE    44 27 363 A1    3/1995

(Continued)

OTHER PUBLICATIONS

Caplus abstract of Moeller (DE 10020445 A1) Nov. 8, 2001.*

(Continued)

Primary Examiner—Alex Noguerola
(74) Attorney, Agent, or Firm—Melanie G. Gover

(57) ABSTRACT

Provided is an electrochemical sensor strip having circuits comprising electrodes in an electrode region connected to contact pads in a contact region by conductive traces wherein the electrode region is off-set from the contact region in both an x direction parallel to the length of the sensor strip and a y direction parallel to the width of the sensor strip. Also provided is a an electrochemical sensor strip having a backing material, an active portion laminated to a portion of the backing material, the active portion comprising a substrate, a circuit comprising electrodes in an electrode region connected to contact pads in a contact region by conductive traces wherein the electrode region is off-set from the contact region in both an x direction parallel to the length of the sensor strip and a y direction parallel to the width of the sensor strip, a polymeric layer comprising a channel-forming material over the electrodes, and a hydrophilic layer over the channel-forming material.

12 Claims, 6 Drawing Sheets

U.S. PATENT DOCUMENTS

| | | |
|---|---|---|
| 6,939,450 B2 * | 9/2005 | Karinka et al. .............. 204/409 |
| 2002/0092612 A1 | 7/2002 | Davies et al. |
| 2003/0088166 A1 | 5/2003 | Say et al. |
| 2003/0102213 A1 | 6/2003 | Gotoh et al. |
| 2003/0200644 A1 | 10/2003 | Matzinger |
| 2003/0203498 A1 | 10/2003 | Neel et al. |
| 2003/0204313 A1 * | 10/2003 | Ou-Yang et al. .............. 702/19 |

FOREIGN PATENT DOCUMENTS

| | | | |
|---|---|---|---|
| DE | 100 20 445 A1 | | 11/2001 |
| EP | 1 152 239 A1 | | 11/2001 |
| EP | 1 203 823 A1 | | 5/2002 |
| JP | 2000-19146 A | * | 1/2000 |
| WO | WO-98/35225 A1 | * | 8/1998 |
| WO | WO 99/13099 | | 3/1999 |
| WO | WO 01/25775 A1 | | 4/2001 |
| WO | WO 02/00918 A2 | | 1/2002 |

OTHER PUBLICATIONS

Search Report for PCT/US2004/033948.

Linder, Erno, Cosofret, Vasile V., Ufer, Stefan and Buck, Richard P.; Kusy, Robert P.; Ash, R. Bruce and Nagle, H. Troy, "Flexible (Kapton-based) Microsensor Arrays of High Stability for Cardiovascular Applications", J. Chem. Soc. Faraday Trans., 1993, vol. 89, pp. 361-367.

Co-pending U.S. Appl. No. 10/702,828, Douglas B. Grundel, filed Nov. 6, 2003.

Co-pending U.S. Appl. No. 10/702,827, Douglas B. Gundel, filed Nov. 6, 2003.

* cited by examiner

CIRCUIT FOR ELECTROCHEMICAL SENSOR STRIP

FIELD

The invention relates to circuits for electrochemical sensors.

BACKGROUND

Electrochemical biosensors have been used to determine a wide range of analyte concentrations for more than three decades. Of particular interest is the measurement of blood glucose levels in patients with diabetes. Products that measure fluctuations in a person's blood sugar, or glucose levels, have become everyday necessities for many of the world's millions of diabetics. Because this disorder can cause dangerous anomalies in blood chemistry and can contribute to vision loss and kidney failure, most diabetics are instructed to test themselves periodically and adjust their glucose level accordingly, usually with insulin injections. Blood glucose levels that are below the normal range may result in reduced blood pressure and loss of consciousness. Blood glucose concentration higher than the normal range can result in coma or stroke. Thus, insulin dependent diabetics may be instructed by their physicians to check their blood glucose several times per day.

Home blood glucose test kits are available to allow the diabetic to have a near normal life style. Typically, these home test kits consist of a lancet for puncturing the skin surface, disposable test strips for collecting the blood sample and a glucose measurement device.

Diabetes produces several common side effects that can make even this routine testing difficult. One of the most common complications of diabetes is diabetic neuropathy and/or nerve damage. Nerve damage can affect an individual's ability to pick-up and handle small items, such a thin, flat test strip sitting on a flat surface. Additionally some diabetics are elderly or are people in general that have difficulty manipulating small objects. Diabetes can also cause eye problems and may lead to blindness. Vision problems can make it difficult to handle the small test strips during both the sample collection step as well as inserting the test strip in the monitor.

The small size and flat profile of most currently available test strips can lead to misuse of the test strips. Also, because many diabetics need to measure their blood glucose levels several times a day any improvements in minimizing the amount of blood needed or reducing the cost of the test strips would be welcome relief.

SUMMARY

One aspect of the present invention features an article comprising an electrochemical sensor strip having circuits comprising electrodes in an electrode region connected to contact pads in a contact region by conductive traces wherein the electrode region is off-set from the contact region in both an x direction parallel to the length of the sensor strip and a y direction parallel to the width of the sensor strip.

Another aspect of the invention features an article comprising an electrochemical sensor strip comprising a backing material, an active portion laminated to a portion of the backing material, the active portion comprising a substrate, a circuit comprising electrodes in an electrode region connected to contact pads in a contact region by conductive traces wherein the electrode region is off-set from the contact region in both an x direction parallel to the length of the sensor strip and a y direction parallel to the width of the sensor strip, a polymeric layer comprising a channel-forming material over the electrodes, and a hydrophilic layer over the channel-forming material.

As used in this application
"active portion" means an area of a sensor strip on which the conductive layer is located;
"inactive portion" means an area of a sensor strip extending from one outside edge to an opposite outside edge on which no part of a conductive layer is located;
"length" means the distance along the broadest dimension;
"width" means the distance along the narrowest dimension.

An advantage of at least one embodiment of the present invention is an electrochemical sensor strip with improved ease of handling.

Another advantage of at least one embodiment of the present invention is a reduction in the cost of an electrochemical sensor strip by using a small circuit without sacrificing ease of handling.

Another advantage of at least one embodiment of the present invention is that the electrode designs allow for smaller, more compact sensor circuits, which in turn will enable sensors requiring smaller sample fluid volumes without sacrificing ease of handling or the ability to introduce sample fluids to the sensor strip.

Other features and advantages of the invention will be apparent from the following drawings, detailed description, and claims.

DETAILED DESCRIPTION

Figure 1:
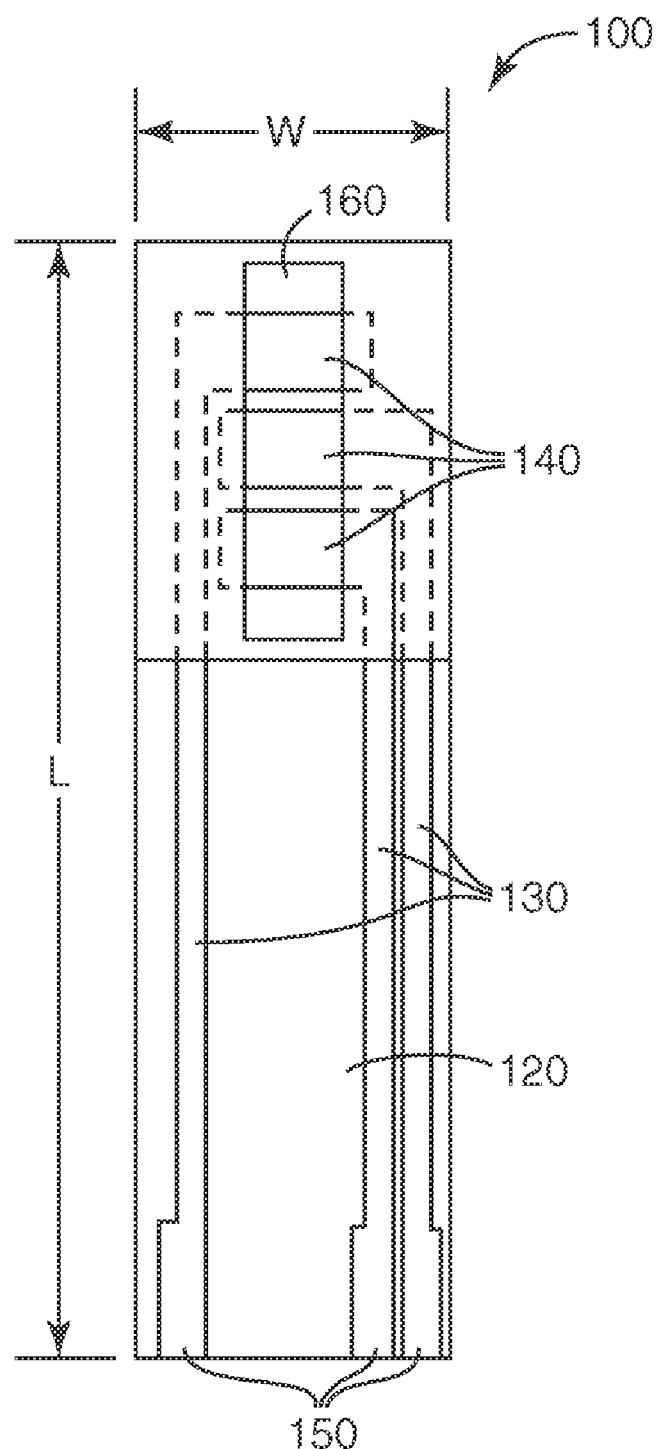
FIG. 1 is a diagram of the typical electrochemical sensor strip available on the market today.

FIG. 1 is a diagram of a portion of a typical electrochemical test strip 100 available on the market today. Additional portions of a test strips might include hydrophilic films, capillary or mesh wicking structures, reagents for analyte detection, and various insulating layers. For an example of a complete test strip construction see, e.g., U.S. Pat. Nos. 4,897,173; 5,997,817; and 5,437,999. The electrochemical test strip has an elongated shape with the electrodes 140 near one end or near the center of the test strip and the contact pads 150 is near the other end. The test strip 100 has a base substrate 120 onto which a conductive layer is deposited. The conductive layer comprises circuit traces 130 running parallel to the long axis of the test strip and connecting the electrodes 140 to the contact pads 150. The contact pads 150 interface with a measurement device (not shown) that measures the electrochemical reaction between the analyte and reagent on the test strip, e.g., a glucose measuring device. A window 160 is defined over the electrodes by the selective placement of an insulating layer over the dielectric substrate and conductive layer. The fluid sample to be tested must be deposited in the window 160, which defines the size of the electrochemical cell. Currently available test strips are generally rectangular in shape. Manually handled strips are about 2.0 cm$^2$ or larger while automated handling strips are about 1.3 cm$^2$ or smaller.

In most cases, the individual strip must be handled by the end user who has to perform various tasks such as removing it from packaging (vial or foil), picking it up from a surface if dropped, inserting it into the analyte measuring device, and disposing of it when finished. Users, particularly those with physical impairments, may have difficulty handling strips that are smaller than about 2.0 cm$^2$. Increased size is synonymous with improved ease of handling. However, a smaller strip would have a lower cost (more strips per area of processed material). This size conflict will become more acute in the future because the cost of materials is anticipated to increase due to needs for increased accuracy with the use of smaller fluid sample volumes.

Both test result accuracy and reduced pain are strong market drivers. Reduced pain is synonymous with smaller fluid sample volumes, e.g., smaller blood samples for a diabetic. However, smaller samples require smaller sensors. Test result accuracy and reduced sensor sizes are driving the need for higher patterning precision of the conductive features as well as non-conductive features on a test strip because smaller sensors require more precise features to produce accurate test results.

At least one aspect of the present invention is a fundamental change in the design and layout of electrochemical sensor strips, in particular glucose sensor strips, that allows a reduction in the amount of costly materials in the strip, but at the same time increases the strip size to enable easy handling. Sensor strips of at least one embodiment of the present invention can be made with an active portion, which requires expensive materials, of less than about 1.4 cm$^2$ and an inactive portion of greater than 2 cm$^2$. This aspect of the invention represents a departure from current industry attempts to reduce cost by reducing the strip size at the expense of manual ease of handling. One way the industry has tried to overcome the reduced ease of handling problem is to use automated strip handling, but these solutions can be costly and may introduce additional problems.

Figure 2A:
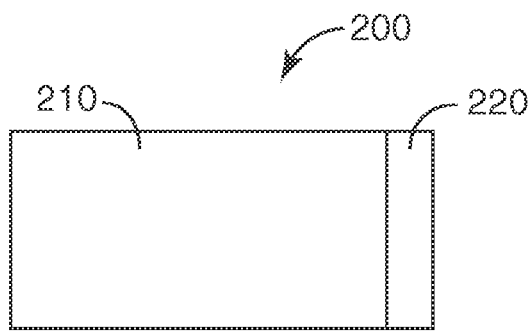
FIGS. 2a-2c shows schematic layouts of three exemplary embodiments of electrochemical sensor test strips of the present invention.
Figure 2B:
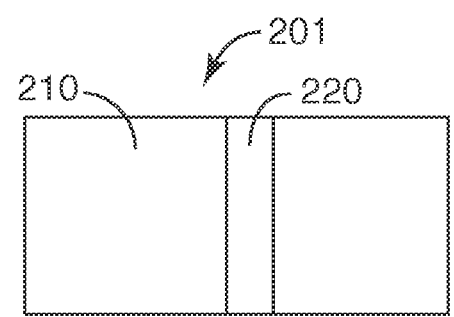
Figure 2C:
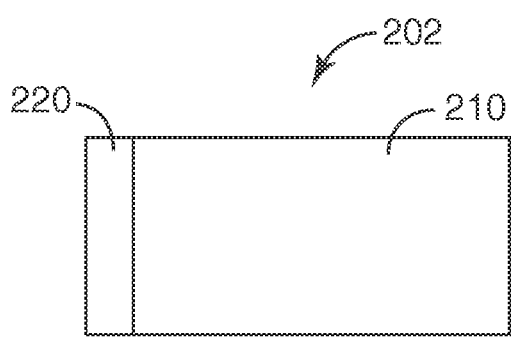

FIGS. 2a-2c illustrates three embodiments of the test strips of the present invention 200, 201, 202, respectively. Each strip comprises a large inactive portion 210, which has no function relative to the electrochemical reading but may be used as a handling tab, which allows the use of inexpensive, unpatterned materials. The tab can be any size, but is typically in the range of about 5 mm to about 25 mm in width and from about 1 cm to about 5 cm length. The active portion 220 of the strip, which requires relatively expensive, precisely patterned materials, may be anywhere on the strip, but is typically at either end or in the middle of the strip. The active portion is typically in the range of about 3 mm to about 10 mm wide and from about 5 mm to about 25 mm long. The active portion can be oriented in any direction, but is typically parallel to the tab orientation, but is typically oriented perpendicular to the tab orientation. Strips of this size without the handling tab would be difficult to handle manually and therefore would suffer from poor market acceptance or would require a costly automated handling system.

Figure 3A:
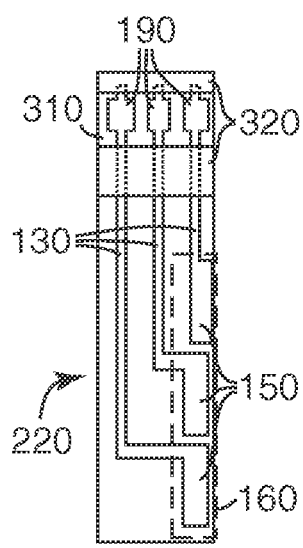
FIGS. 3a-3b shows a close-up view of embodiments of active circuit portions of a sensor strip of the present invention.
Figure 3B:
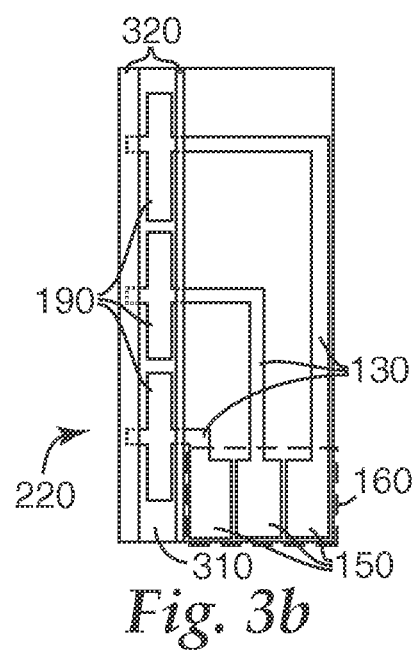

FIGS. 3a and 3b show four possible arrangements for the active portion of the strip including the contact pads, traces and electrodes. FIGS. 3a and 3b as well as FIGS. 5, 6a, 6b, 7, and 8 illustrate unique electrode constructions described in co-pending patent application, U.S. Ser. No. 10/702,828, incorporated in its entirety by reference. The unique electrode constructions have necked portions that reduce the coefficient of variation for electrodes having an area defined by a patterned conductive layer and an overlying patterned insulative layer.

FIG. 3a shows a close-up view of an active portion 220 of a strip that can be bonded to an inactive portion, which can serve as a handling tab. As shown in FIG. 3a, contact pads 150 are connected to electrodes 190 via traces 130. The area in which the contact pads are located is referred to herein as the contact region 160 (indicated by dashed lines). The area in which the electrodes are located is referred to herein as the electrode region. In the embodiments illustrated in FIGS. 3a and 3b, the fluid wicking channel 310 for introducing the fluid sample to the electrodes essentially defines the electrode areas of the circuits. In embodiments of the present invention in which the fluid wicking channel extends to the edges of the sensor strip and is open to the atmosphere on both ends, a fluid sample may be introduced into the wicking channel from either end of the channel with the opposite end of the channel acting as a vent to allow the escape of air that had been occupying the channel prior to introducing the sample. The fluid wicking channel is formed by adding two additional layers to the active portion of the test strip. The first of these layers is an insulating channel-forming spacer material 320, which may be applied as two elongated pieces of material, one along each side of the electrode region (In fact, the channel-forming spacing material defines the electrochemically active area of the electrodes). Useful materials for the channel-forming spacer material include dual-sided adhesive coated films such as medical double coated tapes (available as product number 1512, which has a polyethylene core, and product number 1513, which has a polyester core, from 3M Company, St. Paul, Minn.) or a tri-layer laminate material composed of two layers of a transfer adhesive, which may be an acrylate or rubber-based pressure sensitive adhesive, laminated to a insulating film which may be polyester, polyolefin, polyimide, polyvinylchloride or polycarbonate films.

The required volume of the fluid sample depends on the distance between the two pieces of the channel-forming spacer material and the thickness of the channel-forming spacer material. For some embodiments of the present invention, the required volume is less than 1.0 µl; for other embodiments it is about 0.3 µl. Thin channel-forming spacer material suitable for the present invention typically having a total thickness of about 10 µm to about 200 µm. The top of the fluid wicking channel 310 is formed by laminating a hydrophilic film (not shown) over the top surface of the channel-forming spacer material and the channel. A preferred hydrophilic film is an antifog film (available as product number 9962 from 3M Company, St. Paul, Minn.) having a thickness in the range of about 25 µm to about 200 µm. However, any film material having a suitable hydrophilic surface will suffice. The fluid sample is drawn into the wicking channel by capillary action.

To make a strip with the handling tab even easier to handle, additional features can be added that are not possible with currently available strip designs. The tab may be colored to make it easier to see or it may contain text or graphics (such as logos or directions) that would not fit on a smaller test strip. The handling tab may have a bend or other three-dimensional element.

Figure 4A:
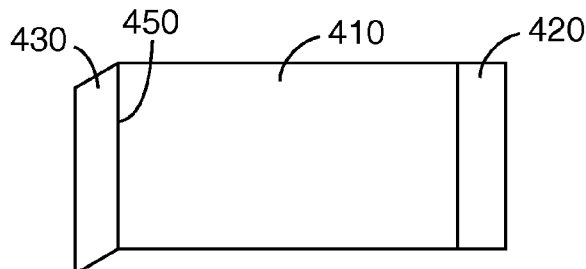
FIGS. 4a-4e show embodiments of sensor strips with handling tabs of the present invention.
Figure 4B:
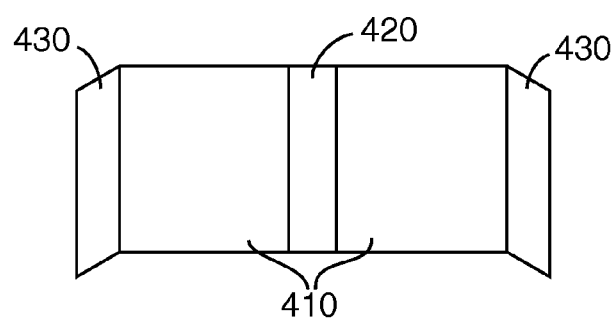
Figure 4C:
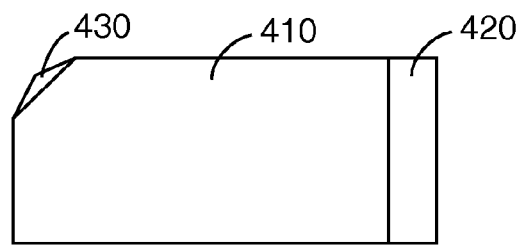
Figure 4D:
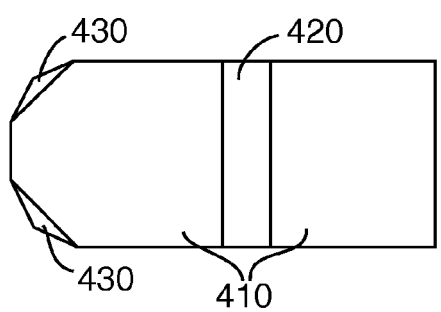
Figure 4E:
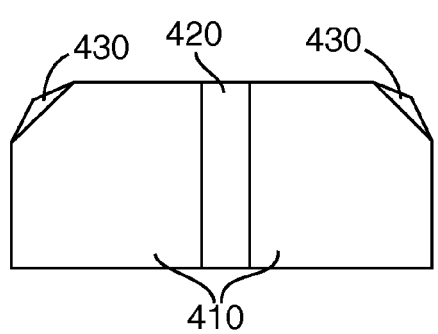

FIGS. 4a-4e show some examples of three-dimensional elements that might increase ease of handling. FIG. 4a shows a sensor strip with transverse demarcation line 450 across the width of the inactive portion 410, which also serves as a handling tab in this instance, indicating a crease or bend that creates bend region 430. When the three-dimensional element or bend is only on one end of the tab, the active portion 420 can be located on any portion of the sensor strip beyond the bend region 430. When a bend is on both ends of the handling tab, the active portion can be located somewhere in the center of the sensor strip. Any useful combination of edge, corner or other bend regions is possible. Depending on the location of the active portion of the test strip the tabs may be bent across the width of the tab or at one or more corners. A bend in the tab allows for easier handling of the strip, particularly if it is dropped by the user and needs to be picked up, or if the user has difficulty removing it from the packaging.

Because conventional test strips have active portions extending along their entire length, bending them could cause trace delamination or fracture of active features. Because the active portions of the strips of the present invention do not need to extend along the entire length of the test strips, bending the test strips is feasible. The bent structures will still allow stacking and easy packing of the strips into a confined space (like a vial) for shipment and storage. One other advantage of a bend in the tab is that it can be used to allow only one way of orienting the strip for insertion into an analyte measuring device. This will enhance the ability to use the strip in low light conditions or if the user has poor eyesight.

In another aspect of the present invention, the backside of the strip can be (micro)textured so the strips can easily be separated from one another. The texturing can also enhance the ease of handling the strips because it causes them to separate more easily when removed from the package. One example of this would be to emboss small features into the backside of the handling tab (i.e., opposite the side that the active portion is on) using microreplication methods such as embossing, thermal stamping, molding imprinting or cast and cure. These methods are described in, e.g., U.S. Pat. Nos. 6,096,247 and 5,820,957.

Figure 5:
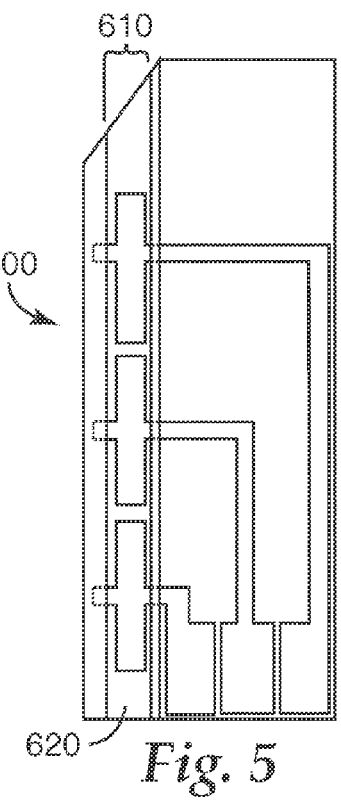
FIG. 5 shows a close-up view of the circuit portion of an electrochemical sensor strip having a fluid sample entrance embodiment of the present invention.

As previously stated, the trend in the industry is to decrease required fluid sample volumes. As these volumes decrease and the active circuit portion of the strip becomes smaller, the sample placement will require increased accuracy. FIG. 5 shows an aspect of the present invention that provides one solution to this problem. An active portion 600 of a test strip (full test strip not shown) has a larger sample entrance 610 to the fluid wicking channel 620 compared with typical strips available on the market today, in which the fluid wicking channel intersects the strip edge at a 90° angle. An aspect of this invention is to employ a fluid wicking channel that has a beveled edge, i.e., intersects the strip edge at an angle that is less than 90°. This can increase the sample entrance without increasing the volume of the channel or fluid sample size. FIG. 5 shows a beveled sample entrance of the present invention that intersects the strip edge at a 45° angle, which results in a sample entrance that is 1.4 times larger than the traditional 90° sample entrance. This increase in the size of the fluid application area should enable easier testing because it makes it easier to get the fluid sample in the fluid wicking channel.

Figure 6A:
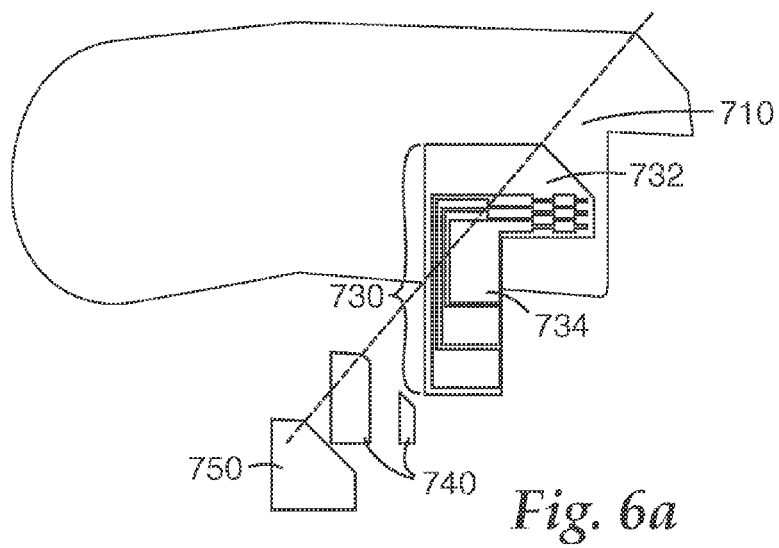
FIGS. 6a-6c are exploded, front, and cross-sectional views, respectively, of one exemplary embodiment of an electrochemical test strip of the present invention.
Figure 6B:
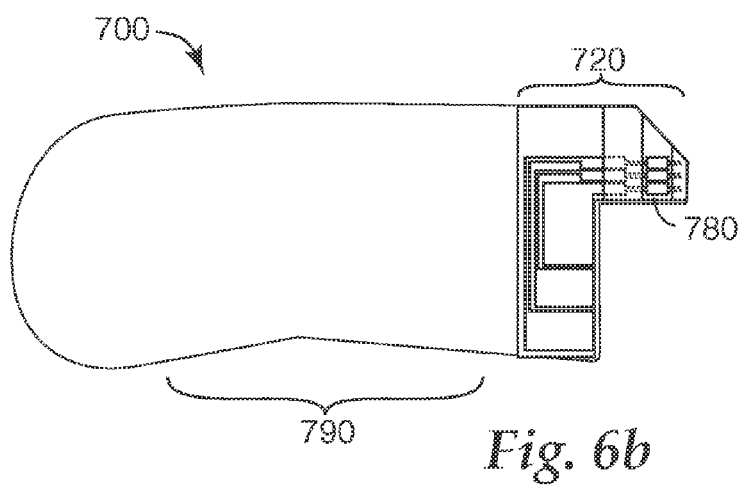
Figure 6C:
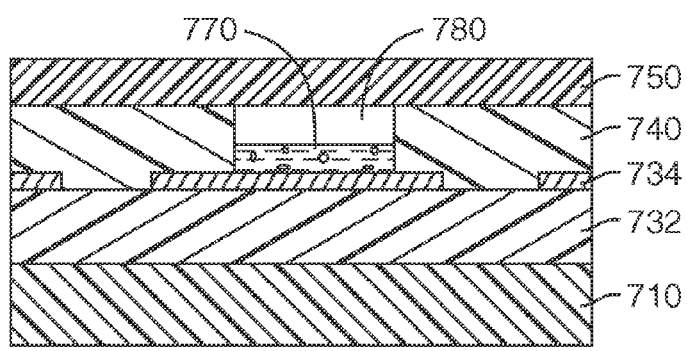

Once the active portion of the strip is built, it can be combined with the remaining materials necessary to build the test strip. Views of one embodiment of a test strip of the present invention are shown in FIGS. 6a-6c. This embodiment of the sensor test strip 700 is comprised of a backing material 710 having an active portion 720 and an inactive tab portion 790. The active portion has a laminate construction comprising a portion of the backing material 710, an adhesive layer (not shown), a circuit portion 730, which includes conductive layer 734, an insulating channel-forming spacer layer 740, at least one reagent layer 770, and a hydrophilic film layer 750. The adhesive layer is adjacent to the backing material 710 and the backside of the circuit portion 730 and may be a transfer adhesive (such as that available under the trade designation 3M Medical transfer adhesive 1524 from 3M, St. Paul, Minn.), although any other suitable adhesive would suffice. The circuit portion 730 is composed of a substrate layer 732 such as polyester, liquid crystal polymer, polyolefin, polyvinylchloride, polyimide, or the like and a conductive layer 734 made from conductive materials such as conductive ink, copper, gold, platinum, palladium, or the like. The conductive layer may be formed by selective deposition patterning, laser ablation, chemical etching, laser scribing, or any other suitable method.

The fluid wicking channel 780, shown in FIGS. 6b and 6c, is formed on the top surface of the circuit portion, centered over the electrodes, by adding two additional layers to the active portion of the test strip. The first of these layers is an insulating channel-forming spacer layer or material 740 applied to the top of the circuit portion 730. Useful materials for the channel-forming space material include dual adhesive coated films such as medical double coated tapes (available as product number 1512, which has a polyethylene core, and product number 1513, which has a polyester core, from 3M Company, St. Paul, Minn.) or a tri-layer laminate material composed of two layers of a transfer adhesive which may be an acrylate or rubber-based pressure sensitive adhesive, laminated to an insulating film which may be polyester, polyolefin, polyimide, polyvinylchloride or polycarbonate films. The volume of the required fluid sample depends on the distance between the two pieces of the channel-forming spacer material and the thickness of the channel-forming spacer material. For some embodiments of the present invention, the required volume is less than 1.0 µl; for other embodiments it is about 0.3 µl. Thin channel-forming spacer material suitable for the present invention typically having a total thickness of about 10 µm to about 200 µm. The second material used to create the fluid wicking is formed by laminating a hydrophilic film 750 on the top surface of the channel-forming spacer material. A suitable hydrophilic film is antifog film (available from 3M Company, St. Paul, Minn. as product number 9962) having a thickness in the range of about 25 µm to about 200 µm. However any film material having a suitable hydrophilic surface will suffice.

In embodiments of the present invention illustrated in FIGS. 6a-6c, the fluid wicking channel extends to the edges of a portion of the sensor strip which portion is narrower than the width of the remainder of the sensor strip. The fluid wicking channel is typically open to the atmosphere on both ends such that a fluid sample may be introduced into the wicking channel from either end of the channel with the opposite end of the channel acting as a vent to allow the escape of air that had been occupying the channel prior to introducing the sample. The fluid can enter the wicking channel by capillary action.

Figure 7:
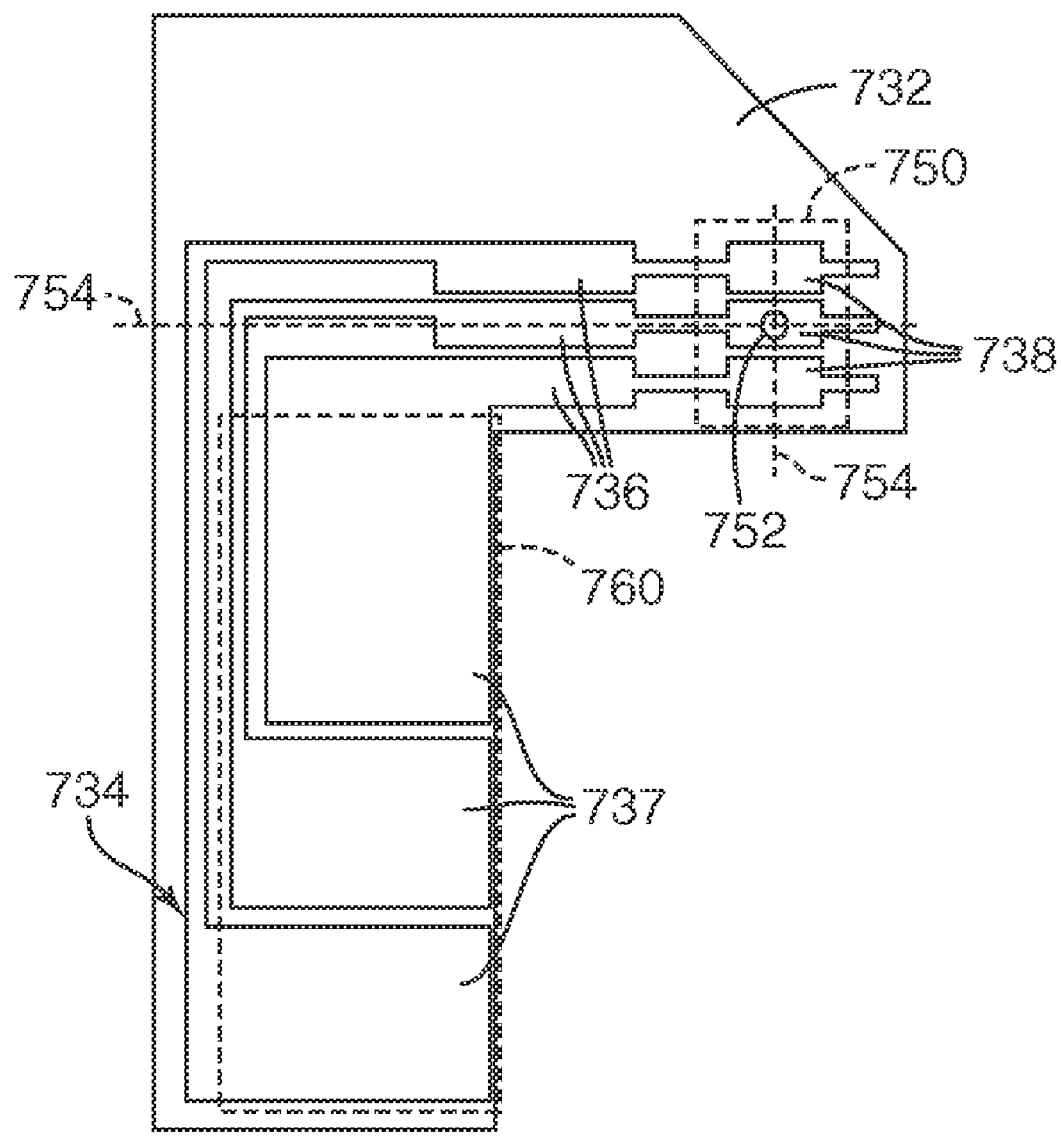
FIG. 7 is a close-up view of an L-shaped circuit embodiment of the present invention.

Another aspect of the invention is a circuit in which the electrode region is off-set from the contact region in both the x and y directions. "Off-set" means that a line bisecting one region, e.g., the electrode region, of a circuit in the x or y direction does not also bisect another region, e.g., the contact region, of the same circuit in the same direction. This concept can be illustrated using FIG. 7. FIG. 7 shows the circuit portion of FIG. 6a. The circuit portion includes substrate 732, electrodes 738 (in electrode region 750) connected to contact pads 737 (in contact region 760) via traces 736. FIG. 7 also shows lines 754 passing through centerpoint 752 of electrode region 750 and extending in the x and y directions. Neither of lines 754, which bisect electrode region 750 in the x and y directions, bisect the contact region 760. The off-set circuit provides a number of advantages when used in combination with an appropriately configured analyte measuring device, such as a glucose measuring device the electrode region, which receives the fluid sample, does not enter, or touch, the measuring device when the contact region is inserted into the measuring device. This avoids the common problem of getting fluids, such as blood, on or in the measuring device. For this aspect of the invention, it is preferable that the contact pads in the contact region extend to the edge of the section of the active portion of the sensor strip that is inserted into the measuring device.

FIGS. 6a-6c (and FIG. 7) show an L-shaped embodiment of an off-set circuit. As can be seen, the contact pads 737 can be inserted into a analyte measuring device while electrodes 738 remain outside the analyte measuring device. An advantage of the L-shaped circuit is that the fluid wicking channel does not extend the entire width of the circuit portion. This results in a reduced fluid sample volume requirement, which allows for the use of a smaller circuit. The L-shaped circuits thus minimizes the size of circuit needed in the test strip. A sensor strip built for ease of handling would be wide, but if the fluid wicking channel extends the width of the strip a larger fluid sample would be required. The L-shape allows a shorter wicking channel, even with a wide sensor strip. As illustrated in FIG. 7, the L-shaped circuit allows for a small electrode area, while still providing a large contact area. This is desirable because the contact portion interfaces with an analyte measuring device and the contact pads need to be large enough to establish a good connection with the conductive features of the measuring device. In addition, the L-shaped circuit achieves the small electrode area and large contact area with short trace elements. This keeps the active portion of the sensor small and cuts down on the use of expensive materials required for the active portion. The L-shaped circuit also prevents contaminating the analyte measuring device when the sensor circuit is inserted to obtain a reading because the electrode area, which receives the fluid sample, is physically separated from the contact area, which is inserted into the measuring device, thereby eliminating or minimizing the likelihood of the analyte sample entering the measuring device. Another possible embodiment of the off-set circuit is a modified-U shape in which the electrode region and contact region are in parallel orientations and the traces connecting them form an arm/base/arm U shapes in which one arm is shorter than the other. FIGS. 3a and 3b illustrate additional off-set circuit embodiments.

Electrochemical sensors of the present invention are useful in glucose monitoring systems. The electrochemical sensors can form a portion of a glucose test strip. A glucose test strip typically comprises a planar substrate, a working electrode and a counter or reference electrode on the substrate, a reagent comprising an enzyme and mediator on the working electrode, and a means for transporting the blood sample to the electrode surface. The electrodes are arranged so that a signal representing the glucose concentration can be generated. After a blood sample is applied onto the working electrode, the test strip (or at least the portion of the test strip containing the contact pads) is inserted into a glucose measuring device such as the blood glucose meter available under the trade name ACCUCHEK ADVANTAGE from Roche Diagnostics Corporation, a division of F. Hoffmann-La Roche Ltd, Basel, Switzerland, which provides a read-out of the glucose level in the blood sample. Glucose monitoring systems are often provided in the form of a kit, which can contain test strips, a glucose measuring device, and optionally a lancet for puncturing the skin to produce a blood sample.

Circuits for electrochemical sensors of the present invention can be made using various known procedures such as metal sputtering, plating, resist laminating, resist exposing, developing, and etching. The sequence of such procedures may be varied as desired for the particular application.

The steps involved in one method of making test strips of the present invention include making the circuit portion, laminating the circuit portion to the tab portion with an adhesive layer, applying channel-forming spacer material on the circuit, laminating a hydrophilic film onto the channel-forming spacer layer to form the fluid wicking channel, and adding handling features (e.g. bending or microstructuring the tab). The circuit portion may be attached to the tab portion with an adhesive (transfer adhesive or a hotmelt adhesive) in a roll-to-roll lamination process. This adhesive can be applied to the back of the circuit portion prior to lamination, or can be applied during the lamination process.

Another process of making sensor strips according to the invention comprises various procedures such as metal sputtering, resist laminating, resist exposing, developing, etching, and plating. The sequence of such procedures may be varied as desired for the particular sensor strip being made.

In a suitable subtractive process, a dielectric substrate is first provided. The dielectric substrate may be a polymer film made of, for example, polyester, polyimide, liquid crystal polymer, polyvinyl chloride, acrylate, polycarbonate, or polyolefin having a thickness of about 10 µm to about 600 µm. The dielectric substrate is sputtered with a seed layer of chrome, nickel-chrome or other conductive metal followed by deposition of the primary conductive layer (e.g. gold (Au), Palladium (Pd), Platinum (Pt), Silver (Ag), Tin (Sn) and alloys thereof). Alternatively, the conductive metal layer may be formed directly on the dielectric substrate without the use of a seed layer. The conductive metal layer can be plated up further to a desired thickness by known electroplating or electroless plating processes.

An aqueous processable negative photoresist is laminated onto at least one side of this bi-layer substrate (i.e. the conductive layer) using standard laminating techniques. The photoresist is then exposed on at least one side to ultraviolet light or the like, through a mask or phototool, crosslinking the exposed portions of the resist. The unexposed portions of the photoresist are then developed with the appropriate, solvent, in the case of aqueous resists a dilute aqueous solution, e.g., a 0.5%-1.5% sodium or potassium carbonate solution, is applied until desired patterns are obtained. The exposed metal is etched away using aqua regia, triiodide-based etchant for Au available from Transene Company Inc., (Danvers, Mass.), as GE-8148 etchant), potassium permanganate or other suitable etchant. The conductive metal layer preferably has a final thickness from about 5 nm to about 200 µm. The resist is then stripped off the circuit in a 2-5% solution of an alkaline metal hydroxide at from about 20° C. to about 80° C., preferably from about 20° C. to about 60° C.

The next step in the process involves placing the channel forming material onto the circuit. The process may include the lamination of a multilayer insulator material, having a release liner on its top surface, to the circuit. This material may be applied as two parallel spaced-apart individual strips of tape, or as a continuous sheet that is later precision cut, e.g., by a rotary die cutting method, to form a wicking channel over exposed electrodes. Alternatively the channel forming material may be formed on the circuit by a selective coating process such as screen printing or inkjet printing or may be a photoimageable material that may be precisely patterned by standard photolithographic techniques.

A suitable test reagent can be applied into the fluid wicking channel of the sensor strip by a known method such as screen printing, injection, slot coating, knife coating, inkjet printing, etc. so that the electrodes are substantially covered by the reagent. The reagent will be selected to test for the desired analyte. Suitable examples of reagents for glucose testing are provided in U.S. Pat. Nos. 5,762,770; 5,288,636; 5,437,999; and 6,287,451 and U.S. Published Patent Application No. 2002/0092612. The reagent typically includes an enzyme, mediator and a buffer. A drying step may be employed to remove solvents and set or activate the reagent if necessary.

The top release liner of the multilayer channel forming material is removed from the build-up structure to provide a clean surface for bonding to a hydrophilic film to complete the formation of the fluid wicking channel.

In order to laminate the active circuit portion to a backing material that will form the inactive portion or handling tab it may be necessary to separate arrays of aligned circuits into double or single-width columns of circuits. A transfer adhesive may be applied to the backside of the active circuit portion and subsequently laminated to the backing material in a continuous roll-to-roll process. The final step in the process may be to form separate sensor strips with separate tabs through a singulation process. An additional step that may be added before or after the singulation step is to bend or crease the backing material to introduce a bend into the backing material. The individual strips can then be packaged as needed for shipment and sale.

Depending on the circuit design, the test strip layout and the requirements, it may be necessary to do converting and auditing steps prior to strip assembly where a sheet of circuits is converted to a smaller format. Other incidental steps may also be included in the process including soaking the film in hot water before or after the etching bath, rinsing steps and the like. Acid baths may also be used as a post-etching neutralization, and web-cleaning steps may follow plating steps.

Another possible method of forming the circuit portion would utilize additive plating and the following typical step sequence:

A dielectric substrate may be coated with a seed layer of chrome, nickel or alloys thereof using a vacuum sputtering technique. A thin first conductive layer of gold, platinum, palladium or alloys thereof is deposited using a vacuum sputtering technique. The materials and thicknesses for the dielectric substrate and conductive metal layer may be as described in the previous paragraphs.

The conductive metal layer can be patterned by a number of well known methods including photolithography, print and etch, laser ablation and laser scribing.

Photoresists, which may be aqueous or solvent based, and may be negative or positive photoresists, are then laminated on at least one side of the metal-coated dielectric substrate using standard laminating techniques with hot rollers. The thickness of the photoresist is from about 12 μm to about 50 μm. The photoresist is then exposed on at least one side to ultraviolet light or the like, through a mask or phototool, crosslinking the exposed portions of the resist. The unexposed portions of the photoresist are then developed with the appropriate solvent, in the case of aqueous resists a dilute aqueous solution, e.g., a 0.5%-1.5% sodium or potassium carbonate solution, is applied until desired patterns are obtained. The first conductive metal layer may then be further plated using standard electroplating or electroless plating methods until the desired circuit thickness in the range of about 5 nm to about 50 μm is achieved.

If desired the dielectric film may be etched to form features in the substrate by applying, crosslinking, and developing a pattern of photoresist, then placing the circuit into a bath of concentrated base at a temperature of from about 50° C. to about 120° C., which etches the portions of the dielectric substrate not covered by the crosslinked resist. This exposes certain areas of the original thin conductive metal layer. Standard electroplating or electroless plating techniques may be used to increase the conductive layer to the desired thickness. The resist is then stripped off both sides of the laminate in a 2-5% solution of an alkaline metal hydroxide at from about 20° C. to about 80° C., preferably from about 20° C. to about 60° C. Subsequently, the original thin first conductive layer is etched where exposed with an etchant that does not harm the dielectric substrate, e.g., a triiodide based etchant for gold (available from Transene Company Inc., (Danvers, Mass.), as GE-8148 etchant). The first conductive metal layer may then be further plated using standard electroplating or electroless plating methods until the desired circuit thickness in the range of about 5 nm to about 50 μm is achieved. Next come converting and auditing steps where the substrate is cut into smaller strips.

Alternatively, a circuit may be formed by coating photoresist from solution onto the gold side of a dual layer substrate comprising a gold layer and a dielectric substrate layer. The protected flexible circuit may be formed by etching the desired pattern into the gold layer in a 43% to 47% concentrated KOH bath or triiodide etchant at 75° C. to 95° C. for about 3-6 minutes. The resist on both sides is then stripped off with 3-4% KOH for 1-2 minutes at 60° C. allowing a clean delamination of the resist from the gold and polyimide surfaces.

After the circuit is formed, two strips of the channel forming spacer material are applied onto the circuit on each side of the electrode region to form the sides of the fluid wicking channel leaving the electrodes exposed on the bottom of the channel. The channel forming spacer material may be provided in the form of a tape having a suitable double-sided release liner or a pre-patterned web having a suitable release line on each side of the web or a dual-sided release liner. The channel forming spacer material may be applied using any number of standard roll-to-roll lamination techniques. In the case where the channel forming spacer material is supplied in the form of a web with two separate release liners, the release liner on the side of the channel forming spacer material to be mated with the surface of the circuit must be stripped off prior to lamination.

Alternatively, a solid layer of the channel forming material can be laminated to the top surface of the circuit portion and then the channels may be cut using either a precise rotary die or kiss cutting method and the surplus material removed.

Next a suitable test reagent can be applied into the fluid wicking channel of the sensor strip by a known method such as screen printing, injection, slot coating, knife coating, inkjet printing, etc. so that the electrodes are substantially covered by the reagent. The reagent will be selected to test for the desired analyte. Suitable examples of reagents for glucose testing are provided in U.S. Pat. Nos. 5,762,770; 5,288,636; 5,437,999; and 6,287,451 and U.S. Published Patent Application No. 2002/0092612. A drying step may be employed to remove solvents and set or activate the reagent if necessary.

After the reagent has been placed into the wicking channel, the release liner is removed to eliminate any overfill or surface contamination leaving a pristine adhesive layer for the addition of the final layer of hydrophilic film. The hydrophilic film is applied on top of the two strips of the channel forming spacer material's adhesive surface to make the topside of the fluid wicking channel. A preferred hydrophilic film is an antifog film (available as product number 9962 from 3M Company, St. Paul, Minn.) having a thickness in the range of about 25 µm to about 200 µm. However any film material having a suitable hydrophilic surface will suffice. The hydrophilic film may be applied using any number of standard roll-to-roll lamination techniques. Finally, the parts are singulated or die cut to produce individual circuit portions or strips of circuit portions which are laminated to a tab portion with the use of a pressure sensitive transfer tape or hot melt adhesive through a lamination procedure. The handling tabs may be bent either before or after final cutting to size.

Figure 8:
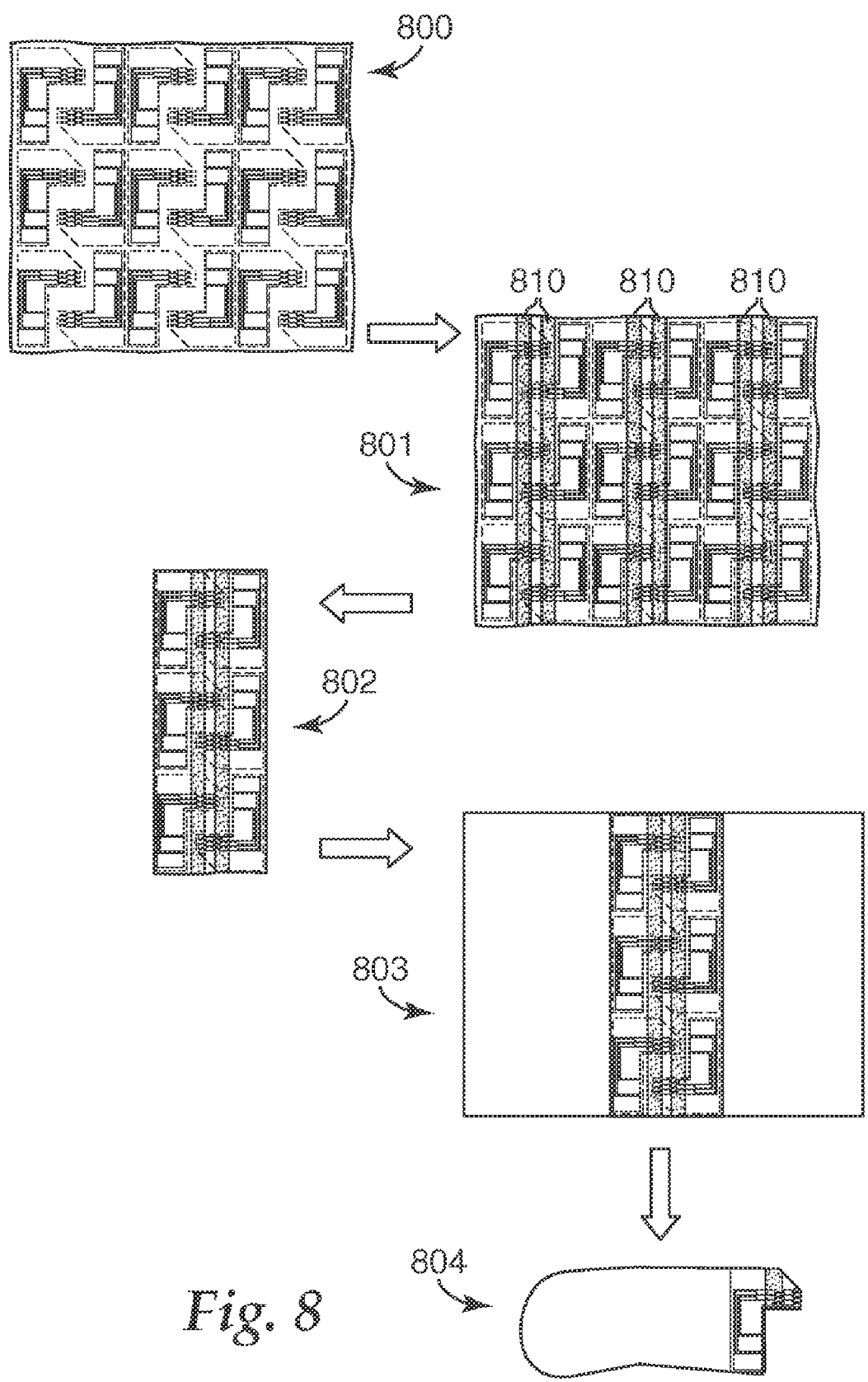
FIG. 8 shows a portion of a method for making sensor strips of the present invention.

FIG. 8 shows a portion of a sensor strip assembly process of the present invention. A portion of a continuous web of nested L-shaped circuits 800 of the type shown in FIG. 7 have individual strips of channel forming material 810 applied in the down web direction to form a continuous web of circuits with defined fluid-wicking channels 801. The web of nested L-shaped circuits is slit into narrower sections having two rows of circuit portions on them 802. These can then be laminated to a backing (tab portion) 803. Application of the reagent and the channel spacer material can be done before or after the formation of the rows of circuit portions depending on the manufacturing process used. Lamination of circuit portions to the tab portions can be done either using separated circuits or using circuit portions still in the sectioned format followed by a final cutting of the strips into individual parts. The tabs may be bent either before or after this final cutting step to produce the final test strip 804.

Various modifications and alterations of this invention will become apparent to those skilled in the art without departing from the scope and spirit of this invention and it should be understood that this invention is not to be unduly limited to the illustrative embodiments set forth herein.

The invention claimed is:

1. An article comprising an electrochemical sensor strip having circuits comprising electrodes in an electrode region connected to contact pads in a contact region by conductive traces wherein the electrode region is off-set from the contact region in both an x direction parallel to the length of the sensor strip and a y direction parallel to the width of the sensor strip, wherein the electrode region and contact region are off-set such that they form an L shape, the interior of which shape forms an edge of the sensor strip and wherein the electrode region protrudes beyond the contact region in the x direction, wherein the circuits are located in an active portion and the article further comprises an inactive portion, and wherein the inactive portion comprises a handling tab.

2. The article of claim 1 wherein the handling tab is bent at one or both ends.

3. The article of claim 1 wherein the handling tab is textured.

4. The article of claim 1 wherein the active portion is about 3 mm to about 10 mm wide and about 5 mm to about 25 mm long.

5. The article of claim 1 wherein the sensor strip is a blood glucose sensor strip.

6. An article comprising a blood glucose test kit comprising the electrochemical sensor strip of claim 5 and a glucose measuring device having a slot that receives the sensor strip article wherein when the sensor strip is fully inserted into the slot the electrode region of the sensor remains outside of the slot.

7. An article comprising an electrochemical sensor strip having circuits comprising electrodes in an electrode region connected to contact pads in a contact region by conductive traces wherein the electrode region is off-set from the contact region in both an x direction parallel to the length of the sensor strip and a y direction parallel to the width of the sensor strip, wherein the electrode region and contact region are off-set such that they form an L shape, the interior of which shape forms an edge of the sensor strip and wherein the electrode region protrudes beyond the contact region in the x direction, wherein the circuits are located in an active portion and the article further comprises an inactive portion, and further comprising a fluid-wicking channel that extends across the length of the electrode region, wherein the fluid-wicking channel terminates at one end with a fluid sample entrance, wherein the fluid sample entrance traverses the end of the fluid-wicking channel at an angle of less than 90, and wherein the length of the electrode region is less than one-half of the width of the circuit.

8. The article of claim 7 wherein the angle is 45.

9. The article of claim 8 wherein the fluid sample entrance is 1.4 times an entrance that intersects the fluid-wicking channel at an angle of 90.

10. The article of claim 7 wherein the fluid-wicking channel is open to the atmosphere at both ends.

11. The article of claim 7 wherein the fluid-wicking channel transports fluid to the electrodes by capillary action.

12. The article of claim 7 wherein the fluid-wicking channel has a volume of less than about one microliter.

* * * * *

UNITED STATES PATENT AND TRADEMARK OFFICE
CERTIFICATE OF CORRECTION

PATENT NO. : 7,419,573 B2  Page 1 of 1
APPLICATION NO. : 10/702344
DATED : September 2, 2008
INVENTOR(S) : Douglas B. Gundel It is certified that error appears in the above-identified patent and that said Letters Patent is hereby corrected as shown below:

Title page,
Item [57], Abstract, Line 7, after "is" delete "a"

Column 8,
Line 55, delete "available" and insert -- (available --, therefore

Column 12,
Line 35, in claim 7, delete "90," and insert -- 90°, --, therefore
Line 38, in claim 8, delete "45." and insert -- 45°. --, therefore
Line 41, in claim 9, delete "90." and insert -- 90°. --, therefore Signed and Sealed this Eighteenth Day of November, 2008

JON W. DUDAS
*Director of the United States Patent and Trademark Office*